United States Patent [19]
Bray et al.

[11] Patent Number: 5,955,266
[45] Date of Patent: Sep. 21, 1999

[54] USE OF PLATELET POLYMORPHISM P1A2 TO DIAGNOSE RISK OF THROMBOTIC DISEASE

[75] Inventors: Paul F. Bray; Pascal J. Goldschmidt-Clermont, both of Baltimore, Md.

[73] Assignee: The Johns Hopkins University School of Medicine, Baltimore, Md.

[21] Appl. No.: 08/626,023

[22] Filed: Apr. 1, 1996

[51] Int. Cl.⁶ .............................. C12Q 1/68; C07H 21/04; C12P 19/34
[52] U.S. Cl. ................... 435/6; 536/24.3; 935/8; 935/77; 935/78; 435/91.2
[58] Field of Search .................. 435/6, 91.2, 810; 935/8, 77, 78; 536/23.1, 24.33, 24.3

[56] References Cited

U.S. PATENT DOCUMENTS 5,091,302  2/1992  Newman et al. ...................... 435/6

OTHER PUBLICATIONS

Dorland's Illustrated Medical Dictionary, W.B. Saunders Co., Philadelphia (1994) pp. 1706–1708, 1994.
Stratagene Catalog (1988) p. 39, 1988.
McFarland et. al. Blood 78: 2276–2282 (Nov. 1991).
Wang et. al. The Journal of Clinical Investigation 90:2038–2043 (Nov. 1992).
Weiss et al Circulation 92: I–30 abstract 0138 (Oct. 1995).
Jin et. al. Blood 82:2281–2288. (Oct. 1993).
E. J. Weiss, et al., A monoclonal antibody (SZ21) specific for platelet GPIIa distinguishes $Pl^{A1}$ from $Pl^{A2}$, Tissue Antigens 1995: 46: pp. 374–381.
Paul F. Bray et al., Rapid Genotyping of the Five Major Platelet Alloantigens by Reverse Dot–Blot Hybridization, Blood, vol. 84, No. 12, Dec. 12, 1994, pp. 4361–4367.

*Primary Examiner*—W. Gary Jones
*Assistant Examiner*—Debra Shoemaker
*Attorney, Agent, or Firm*—Fish & Richardson, P.C.

[57] ABSTRACT

A method for diagnosing a subject having or at risk of having a thrombotic disease syndrome by analysis of a platelet polymorphism is provided. The association between a polymorphism of the $Pl^{A2}$ allele of the GPIIIa gene and unstable thrombotic syndromes provides the basis for methods and kits for diagnosing subjects.

20 Claims, 2 Drawing Sheets

USE OF PLATELET POLYMORPHISM P1A2 TO DIAGNOSE RISK OF THROMBOTIC DISEASE

STATEMENT AS TO FEDERALLY SPONSORED RESEARCH

Support for the research herein was provided by the United States Government as NIH grants HL49762, HL49748 and NR02241. The U.S. Government has certain rights in this invention.

FIELD OF THE INVENTION

The present invention relates generally to platelet antigens and specifically to a method for diagnosing risk of thrombotic associated syndromes based on a polymorphism in glycoprotein IIIa antigen.

BACKGROUND OF THE INVENTION

Heart disease is one of the leading causes of death in adults. Its prevalence has been linked with aging and a number of environmental and dietary risk factors, such as lack of exercise, consumption of high levels of saturated fat, and lack of antioxidants in the diet. However, every year, individuals who do not fit these established risk profiles fall victim to the disease in its many forms. Especially puzzling are those cases of heart disease among relatively young persons, for example persons under 60 years of age.

It is known that formation of a platelet aggregate at the site of a ruptured coronary plaque is implicated in the pathogenesis of myocardial infarction (MI)and unstable angina (USA) (Y. Jang et al., *J. Am Coll. Cardiol.* 24:1591–1601, 1994; N. A. Flores et al., *Cardiovasc. Res.* 28:295–302, 1994; Chandler, et al., *Amer J Card.* 34:823, 1974; Fuster, et al., *N Engl J Med,* 3:242, 1992; DeWood, et al., *N Engl J Med.,* 31:417, 1986). Formation of platelet aggregates requires binding of fibrinogen, and in some situations, von Willebrand factor, to the glycoprotein IIb-IIIa (GPIIb-IIIa) receptor. Over the past ten years, large trials of various inhibitors of platelet function, such as aspirin and antibodies, particularly monoclonal antibody directed against the platelet GPIIb/IIIa receptor complex, have demonstrated a significant benefit both in preventing and in reducing the mortality and morbidity of unstable coronary syndromes such as MI, USA, and restenosis after angioplasty. Additional studies have linked ex vivo platelet reactivity to outcome in post-MI patients (M. D. Trip et al., *N. Engl. J. Med.* 322:1549–54, 1990).

The fibrinogen receptor, GPIIb-IIIa, has been studied in connection with alloimmune-mediated platelet destruction by antibodies to platelet-specific antigens in well-known clinical conditions, including neonatal alloimmune thrombocytopenia, posttransfusion purpura, and refractoriness to platelet transfusions. These studies have resulted in the discovery that amino acid substitutions in platelet membrane glycoproteins result in formation of alloantigens. Thus, identification of these and other polymorphisms in cell surface glycoproteins is important in the study of pathogenesis of alloimmune-mediated disorders.

Platelet membrane glycoproteins are highly polymorphic, and can be recognized as allo- or self-antigens. Five major platelet alloantigen systems have now been identified. Incompatibility of epitopes on the various platelet surface glycoproteins has been recognized as responsible for the alloimmune thrombocytopenias; most commonly, these syndromes of immune mediated platelet destruction are induced by alloantibodies against the $Pl^A$ alloantigen on GPIIIa(P. J. Newman et al., J. Loscalzo et al., eds. Blackwell Scientific Publications, Cambridge, Mass., 1994, 529–54).

The DNA polymorphisms responsible for the five major platelet alloantigen systems have now been identified and are summarized in Table 1 below. In all cases, a single nucleotide substitution results in an amino acid change that, in turn, alters the antigenicity of the glycoprotein. The molecular basis for the $Pl^{A1}/Pl^{A2}$ polymorphism, which is responsible for immune mediated platelet destruction in humans, is characterized by a difference in a single amino acid at residue 33 of the mature GPIIIa protein. $Pl^{A1}$ has a leucine at position 33 of the mature GPIIIa; while $Pl^{A2}$ has a praline at this position as the result of a T to C nucleotide substitution at nucleotide 156 of the GPIIIa gene.

TABLE 1

Human Platelet Alloantigens

| Alloantigen | Glycoprotein | Location |
| --- | --- | --- |
| $Pl^{A1}$, $Zw^a$ | IIIa | Leucine/33 |
| $Pl^{A2}$, $Zw^b$ | IIIa | Proline/33 |
| $Ko^b$ | Ib | Threonine/145 |
| $Ko^a$ | Ib | Methionine/145 |
| $Bak^a$, $Sib^a$ | IIb | Isoleucine/843 |
| $Bak^b$, $Sib^a$ | IIb | Serine/843 |
| $Pen^a$, $Yuk^b$ | IIIa | Arginine/143 |
| $Pen^b$, $Yuk^a$ | IIIa | Glutamine/143 |
| $Br^b$, $Zav^b$ | Ia | Glutamic acid/505 |
| $Br^a$, $Zav^a$ | Ia | Lysine/505 |

SUMMARY OF THE INVENTION

The present invention is based on the discovery of a high prevalence of the platelet GP IIIa polymorphism $Pl^{A2}$ among individuals with myocardial infarction and unstable angina. The discovery that the $Pl^{A2}$ polymorphism is an inherited marker indicating increased susceptibility for 10 development of thrombotic disease syndromes, provides a basis for employing more accurate diagnostic, prognostic, preventative and therapeutic regimes in individuals heterozygous or homozygous for the polymorphism $Pl^{A2}$.

The invention provides isolated allele specific oligonucleotides useful for diagnosis of a subject having, or at risk of having, a thrombotic disease syndrome, e.g., heart disease. The invention also provides a method for diagnosis of such subjects by contacting target nucleic acid of a sample from the patient with a reagent that detects the polymorphism $Pl^{A2}$, and detecting the presence of the polymorphism.

BRIEF DESCRIPTION OF THE DRAWINGS

FIG. 3A is a restriction map of GPIIIa exon 2, undigested fragments, and digestion products resulting when $Pl^{A1}$ or PlA2 PCR products are reacted with the restriction enzymes MspI and NciI. Sizes of fragments (in base pairs) are indicated below the horizontal lines. Vertical bars indicate the ends of PCR fragments or digestion products. For clarity and because it does not cause a detectable change in the fragment sizes, an additional MspI site (present in both PlA alleles) 7 base pairs from the 3' MspI site is not shown.

FIG. 3B is a photograph of a representative ethidium stained 3% agarose gel showing PCR products for patients corresponding to the three possible allelic combinations: PlA1/A1 (lanes 1–3); Pl$^{A1/A2}$ (lanes 5–7); and Pl$^{A2/A2}$ (lanes 8–10). Undigested PCR products are shown in lanes 1, 5, and 8; MspI digested products are shown in lanes 2, 6, and 9); and NciI digested products are shown in Lanes 3, 7, and 10. Lane 4 contains ΦX174 DNA cut with HaeIII as a size marker.

FIG. 3C summarizes the results of reverse dot blot hybridization analysis performed on the same patients as in FIG. 3B. Hybridization specific for Pl$^{A1}$ shown on the top row and hybridization specific for Pl$^{A2}$ is shown on the bottom row.

A DETAILED DESCRIPTION OF THE INVENTION

Figure 1:
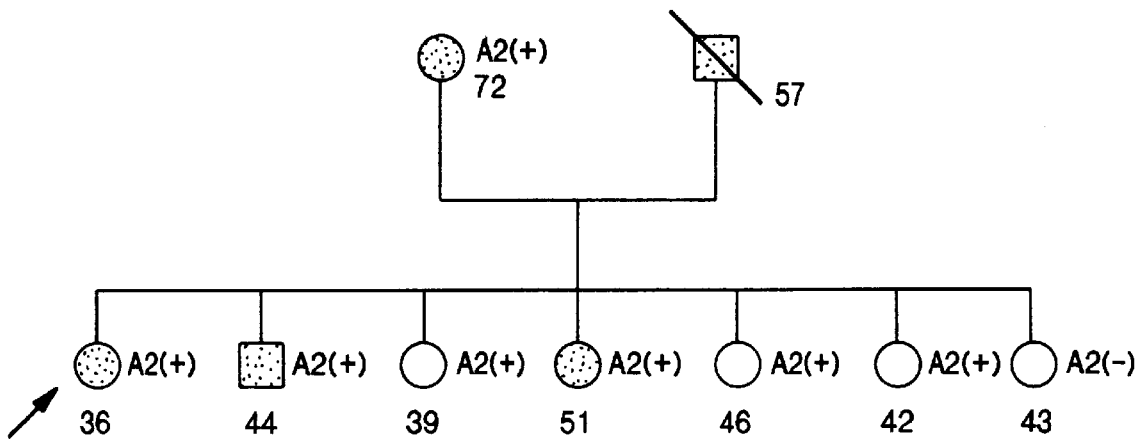
FIG. 1 is a schematic representation of the pedigree of kindred PT1. Squares denote male family members, and circles denote female family members. Shaded symbols indicate individuals with premature coronary heart disease. Deceased members are indicated by a slash. The age of each member is indicated beneath the representative symbol. $Pl^{A2}$ positivity (i.e., PlA2/A2 or PlA2/A1 is denoted by "A2(+)"; "A2(−)" denotes PlA negativity (PlA1/Al). The arrow indicates the proband.

The present invention relates to methods for identifying individuals at risk for thrombotic disease, including arterial or vascular thrombotic disease, and specifically to a polymorphism in the fibrinogen receptor, glycoprotein IIb-IIIa (GPIIb-IIIa), that is associated with susceptibility for thrombotic syndromes, e.g., coronary heart disease. As used herein, the term "thrombotic disease" or "thrombotic syndrome" refers to all vascular thrombotic diseases, both arterial and venous. Such diseases include but are not limited to cerebrovascular disease (stroke), coronary artery disease, myocardial infarction, and venous or arterial thrombosis at locations remote from the heart or head.

The present invention is based upon the identification of an inherited risk factor for the development of thrombotic disease syndromes, such as acute coronary artery thrombosis, myocardial infarction (MI) and unstable angina (USA). It has been discovered that, in comparison with various control groups, the group of individuals with myocardial infarction and unstable angina shows an increase in the frequency of platelet GPIIIa polymorphism Pl$^{A2}$. The increased mortality at a younger age in subjects homozygous for the mutation is likely due to the earlier onset of heart disease.

Among Caucasians in the population at large, the frequency of the Pl$^{A1}$ polymorphism is more than five times that of the Pl$^{A2}$ polymorphism. For instance, both immunophenotyping and genotyping of northern European Caucasians demonstrated the gene frequency for Pl$^{A1}$ and Pl$^{A2}$ as 85% and 15%, respectively. Among 71 Caucasians in several ethnic groups in the United States the gene frequencies for Pl$^{A1}$ and Pl$^{A2}$ were 89% and 11%, respectively. By contrast, it has been discovered that, in a kindred (PT1) in which there is a high prevalence of premature coronary heart disease, the platelet polymorphism PlA is much higher than in the general population, even among Caucasians. In Caucasian patients with MI or USA as compared to two different Caucasian control groups, the Pll gene frequency was 2.3 and 3.3 times that found in the control groups. Further analysis of the data has revealed that the influence was greatest in those subject with early onset of disease, a characteristic finding consistent with the phenotype of an inherited risk factor. In fact, half of the patients studied with a first event of MI or USA before the age of 60 were Pl$^{A2}$ positive. It is particularly noteworthy that five of the patients with either MI or USA (MI/USA) were homogygous Pl$^{A2/A2}$. Since the expected frequency of Pl$^{A2}$ homozygosity is 2%; among Caucasians, 250 individuals (nearly 3.6 times the number of MI/USA patients studied) from the general population would need to be studied to detect five who were Pl$^{A2}$ homozygotes. A lower frequency of Pl$^{A2}$ has been demonstrated outside the Caucasian sub-group.

These findings demonstrate a strong association between the Pl$^{A2}$ allele and unstable thrombotic syndromes and is the first identification of an inherited platelet risk factor for thrombotic disease. The mechanism by which the presence of the Pl$^{A2}$ polymorphism alters the frequency of the thrombotic event is unknown. However, while not wanting to be bound by a particular theory, it is believed that the presence of this polymorphism alters the adhesive properties of platelets and/or endothelial cells, and/or smooth muscle cells. The GPIIb-IIIa complex is a prototypic member of the integrin super-family of adhesive molecules (E. F. Plow et al., *J. Am. Coll. Cardiol.* 24:1591–1601, 1994) and serves as the major platelet receptor for fibrinogen. In areas of high shear stress (in arterial circulation), GPIIb-IIIa also possesses major von Willebrand factor binding activity (Y. Ikeda et al., *J. Clin. Invest.* 87:1234–1240, 1991). Therefore it is believed that a substitution of proline for leucine at amino acid 33 of mature GPIIIa in platelets and/or endothelial cells enhances receptor adhesiveness to fibrinogen and/or von Willebrand factor, in a pro-thrombotic manner. Such a mechanism is consistent with the known important role of GPIIb-IIIa in the pathogenesis of unstable coronary events (J. Lefkovits et al., *N. Engl. J. Med.* 3:1553–9, 1995).

Recent studies indicate that treatment of unstable coronary syndromes with aspirin therapy or with specific inhibitors of GPIIb-IIIa improves outcomes. Therefore the identification of Pl$^{A2}$ positive patients may be used to make informed decisions regarding selection of therapies, such as anti-GPIIb-IIIa therapy, designed to treat and/or forestall development of heart disease.

In a first embodiment, the present invention provides isolated allele specific oligonucleotides (ASOs) for diagnosis of a subject having or at risk of having thrombotic disease syndromes, wherein the oligonucleotide hybridizes with a target polynucleotide sequence having substantially the sequence selected from the group consisting of 5'-CCTGCCTCZGGGCTCAC-3' (SEQ ID NO:1) and 5'- TGCCTCCGGGCTCACC-3' (SEQ ID NO:2) and sequences substantially complementary thereto.

The allele specific oligonucleotides were produced based upon identification of regions within the GPIIIa gene encoding the polymorphism Pl$^{A2}$. The term "sequences substantially complementary thereto" or "substantially the sequence" refers to sequences which hybridize to the sequences provided (e.g., SEQ ID NO:1 and SEQ ID NO:2) under stringent conditions. The term "isolated" or "purified" as used herein includes oligonucleotides substantially free of other nucleic acids, proteins, lipids, carbohydrates or other materials with which they may be naturally associated. A "target polynucleotide" refers to the nucleic acid sequence of interest, e.g., the Pl$^{A2}$ polymorphism encoding polynucleotide.

The position of the point mutations at codon 33 are in bold and are underlined as in the sequence shown herein. Those of skill in the art can design appropriate allele specific oligonucleotides for identification of such a mutation. Preferably, the ASOs of the invention have substantially the sequence 5'- GTGAGCCCAGAGGCAGG-3' (SEQ ID NO:3) or
5'-GGTGAGCCCGGAGGCA-3' (SEQ ID NO:4).

Preferably, the primers of the invention which hybridize to the upstream and downstream (e.g., flanking) sequences of the GPIIIa gene so as to bracket the polymorphism locus have the nucleotide sequence 5'-TTCTGATTGCTGGACTTCTCTT-3' (sense)(SEQ ID NO:5)and 5'-TCTCTCCCCATTGGCAAAGAGT-3' (antisense) (SEQ ID NO:6).

The primers of the invention embrace oligonucleotides of sufficient length and appropriate sequence so as to provide specific initiation of polymerization on a significant number of nucleic acids flanking the polymorphic locus. Specifically, the term "primer" as used herein refers to a sequence comprising two or more deoxyribonucleotides or ribonucleotides, preferably more than three, and most preferably more than 8. Environmental conditions conducive to synthesis include the presence of nucleoside triphosphates and an agent for polymerization, such as DNA polymerase, and a suitable temperature and pH. The primer is preferably single stranded for maximum efficiency in amplification. Preferably, the primer is an oligodeoxyribonucleotide. The primer must be sufficiently long to prime the synthesis of extension products in the presence of the inducing agent for polymerization. The exact length of primer will depend on many factors, including temperature, buffer, and nucleotide composition. The oligonucleotide primer typically contains 12–20 or more nucleotides, although it may contain fewer nucleotides.

Primers of the invention are designed to be "substantially" complementary to each strand of the genomic locus to be amplified. This means that the primers must be sufficiently complementary to hybridize with their respective strands under conditions which allow the agent for polymerization to perform. In other words, the primers should have sufficient complementarity with the 5' and 3' sequences flanking the codon 33 mutation of GPIIIa to hybridize therewith and permit amplification of the polymorphic locus.

The oligonucleotide primers of the invention may be prepared using any suitable method, such as conventional phosphotriester and phosphodiester methods or automated embodiments thereof. In one such automated embodiment, diethylphosphoramidites are used as starting materials and may be synthesized as described by Beaucage, et al. (*Tetrahedron Letters,* 22:1859–1862, 1981). One method for synthesizing oligonucleotides on a modified solid support is described in U.S. Pat. No. 4,458,066.

Any nucleic acid specimen, in purified or nonpurified form, can be utilized as the starting nucleic acid or acids, provided it contains, or is suspected of containing, the specific nucleic acid sequence containing the polymorphic locus. Thus, the process may employ, for example, DNA or RNA, including messenger RNA, wherein DNA or RNA may be single stranded or double stranded. In the event that RNA is to be used as a template, enzymes, and/or conditions optimal for reverse transcribing the template to DNA would be utilized. In addition, a DNA-RNA hybrid which contains one strand of each may be utilized. A mixture of nucleic acids may also be employed, or the nucleic acids produced in a previous amplification reaction herein, using the same or different primers may be so utilized. The specific nucleic acid sequence to be amplified, i.e., the polymorphic locus, may be a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as contained in whole human DNA.

DNA utilized herein may be extracted from a body sample, such as blood, tissue material and the like by a variety of techniques such as that described by Maniatis, et al. (*Molecular Cloning: A Laboratory Manual,* Cold Spring Harbor, N.Y., pp 280, 281, 1982). If the extracted sample is impure, it may be treated before amplification with an amount of a reagent effective to open the cells, or animal cell membranes of the sample, and to expose and/or separate the strand(s) of the nucleic acid(s). This lysing and nucleic acid denaturing step to expose and separate the strands will allow amplification to occur much more readily.

Sequences amplified by the methods of the invention can be further evaluated, detected, cloned, sequenced, and the like, either in solution or after binding to a solid support, by any method usually applied to the detection of a specific DNA sequence such as PCR, oligomer restriction (Saiki, et al., *Bio/Technology,* 3:1008–1012, 1985), allele-specific oligonucleotide (ASO) probe analysis (Conner, et al., *Proc. Natl. Acad. Sci. USA,* 80:278, 1983), oligonucleotide ligation assays (OLAs) (Landegren, et al., *Science,* 241:1077, 1988), restriction endonuclease analysis and the like. Molecular techniques for DNA analysis have been reviewed (Landegren, et al., *Science,* 2:229–237, 1988).

The amplified product may be detected by analyzing via a Southern blotting technique or similarly, using dot blot analysis. Suitable solid supports useful in Southern blotting techniques are membranes, beads, microtiter plates, etc. The use of non-radioactive probes or labels is facilitated by the high level of the amplified signal. Alternatively, probes used to detect the amplified products can be directly or indirectly detectably labeled. A detectable label is one that can be detected by physiochemical means, such as with a radioisotope, a fluorescent compound, a bioluminescent compound, a chemiluminescent compound, by color absorbance, a metal chelator or an enzyme. Those of ordinary skill in the art will know of other suitable labels for binding to the probe, or will be able to ascertain such, using routine experimentation.

The nucleic acid probe is preferably labeled with a compound that allows detection and/or quantitation of binding of the probe to the polymorphic locus to determine whether the person is a normal homozygote, heterozygote, or homozygote for the mutation. A nucleic acid probe specific for detection of the codon 33 mutation of leucine to proline as a result of a T to C nucleotide substitution at position 1565 of the GPIIIa gene is preferred. Such a probe binds to codon 33 and nucleotides flanking the codon. Any specimen containing a detectable amount of the DNA comprising the polymorphic locus can be used. Preferably the subject is human.

In a preferred aspect of the invention, the $Pl^{A2}$ polymorphism is detected by the reverse dot blot hybridization technique (RDB) (see for example, Bray, et al., *Blood,* 84(12):4361, 1994, incorporated herein by reference). Briefly, allele-specific oligonucleotides as exemplified by SEQ ID NO:3 and SEQ ID NO:4, are fixed to a solid support (e.g., a filter). Typically, an amino group is added to the terminus of the ASO for covalent attachment to the support. Labeled (e.g., biotinylated) oligonucleotides flanking the polymorphic sequence in genomic DNA (e.g., SEQ ID NO:1 and SEQ ID NO:2) are used to amplify genomic DNA by PCR, for example, and these PCR products are denatured into single stranded DNA and hybridized to the filters containing the ASOs. Preferably, RDB, as described in the method of the invention, is performed using enzymatic labels and a colormetric assay. RDB is specific, sensitive and rapid for the detection of $Pl^{A2}$ polymorphisms.

Because the ASOs are previously applied to the membranes, or other solid support, the entire procedure can be performed in one day, with the DNA extraction requiring about 1 hour, the PCR reaction requiring about 2 to 3 hours, the hybridization reaction requiring 1 to 2 hours; and the washing and color development requiring about 1 hour. It is possible to obtain enough DNA to conduct a reverse dot blot genotyping of platelet alloantigens from as little as 5 µl of whole blood.

Preferably, the method of amplifying is by PCR, as described herein and as is commonly used by those of ordinary skill in the art. Alternative methods of amplification have been described and can also be employed as long as the polymorphic locus amplified by PCR using the primers of the invention is similarly amplified by the alternative means.

In another aspect of the invention, the $Pl^{A2}$ polymorphism is detected by restriction endonuclease analysis. Specifically, the mutation at codon 33 of GPIIIa creates a new restriction endonuclease site which is distinguishable from an allele not having the mutation. The wild-type allele including codon 33, has a sequence 5'-CCTGCCTC<u>T</u>GGGCTCAC-3' (SEQ ID NO:1), whereas the $Pl^{A2}$ polymorphism has a sequence 5'- TGCCTC<u>C</u>GGGCTCACC-3' (SEQ ID NO:2). The point mutation of T-C creates a restriction endonuclease site CC↓(G/C)G. Enzymes such as MspI and NciI, for example, have such a recognition site and are able to cut the genomic DNA having the polymorphism, but not the wild-type allele. Other enzymes having similar recognition sites will be known to those of skill in the art.

In another aspect, the invention provides a method for diagnosis of a subject, particularly a subject 60 years old or younger, based on the determination of whether the subject is heterozygous or homozygous for the mutation. Those being normal, or wild-type homozygotes ($Pl^{A1}/Pl^{A1}$), heterozygotes ($Pl^{A1}/Pl^{A2}$) and homozygotes ($Pl^{A2}/Pl^{A2}$) for the mutation will have respectively increasing susceptibility to, i.e. an increasing risk of developing thrombotic disease, premature stroke, and associated complications, especially developing such conditions under the age of 60 years.

As used herein, the term "normal homozygote" or "wild-type homozygote" means a subject having a sequence as in SEQ ID NO:1, (both of the $Pl^{A1}$ alleles). The frequency of normal homozygotes can be determined by statistical demographic data for the general population, or for the ethnic subgroup to which the subject belongs. For instance, a sample from a Caucasian would be compared with the statistical norm for a Caucasian subgroup of the general population. A heterozygote would exhibit a mutation at codon 33 in the $Pl^{A2}$ allele ($Pl^{A1}/Pl^{A2}$), while a homozygote for the mutation would have the mutation in both alleles ($Pl^{A2}/Pl^{A2}$).

In another embodiment, the invention provides a kit useful for the diagnosis of a subject having or at risk of having a thrombotic disease. The kit contains a container containing oligonucleotide primers for amplification of $Pl^{A}$ of the GPIIIa gene. The kit may further contain allele specific oligonucleotides (ASO) for the detection of a $Pl^{A2}$ polymorphism. For example, the exemplary ASOs of the invention, 5'- GTGAGCCCAGAGGCAGG-3' (SEQ ID NO:3) and 5'-GGTGAGCCCGGAGGCA-3' (SEQ ID NO:4) may be included in the kit.

One skilled in the art will appreciate that standard techniques of immunologic analysis can also be used as the basis for the diagnostic tests of the invention. In such techniques, alloantibodies to the $Pl^{A2}$ polymorphism are detected by measuring alloantibody binding to a panel of typed platelets. This technique requires the availability of well-characterized typing sera and a panel of phenotyped donors. Commercially available monoclonal antibodies specific for $Pl^{A1}$, such as SZ21 (Immunotech, Westbrook, Me.), can be used to distinguish A1/A1 from A2/A2 platelets, for example. Further, as demonstrated in the present examples, flow cytometric or Western blot analysis are useful for distingusihing Pl polymorphisms.

Therefore in another embodiment, the invention provides a kit useful for the diagnosis of a subject having or at risk of having a thrombotic disease. The kit contains an antibody which detects a $Pl^{A2}$ polymorphism in the GPIIIa gene.

Monoclonal antibodies useful for immunophenotyping for $Pl^{A2}$ are suited for use, for example, in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and non-competitive immunoassays in either a direct or indirect format. Examples of such immunoassays are the radioimmunoassay (RIA) and the sandwich (immunometric) assay. Detection of the platelet antigens using monoclonal antibodies can be done utilizing immunoassays which are run in either the forward, reverse, or simultaneous modes, including immunohistochemical assays on physiological samples (e.g., blood). Those of skill in the art will know, or can readily discern, other immunoassay formats without undue experimentation.

The term "immunometric assay" or "sandwich immunoassay", includes simultaneous sandwich, forward sandwich and reverse sandwich immunoassays. These terms are well understood by those skilled in the art. Those of skill will also appreciate that antibodies as described herein will be useful in other variations and forms of assays which are presently known or which may be developed in the future. These are intended to be included within the scope of the present invention.

Monoclonal antibodies can be bound to many different carriers and used to detect the presence and phenotype of $Pl^{A}$ platelet antigens. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such using routine experimentation.

In performing the assays it may be desirable to include certain "blockers" in the incubation medium (usually added with the labeled soluble antibody). The "blockers" are added to assure that non-specific proteins, proteases, or anti-heterophilic immunoglobulins to anti-Pl immunoglobulins present in the experimental sample do not cross-link or destroy the antibodies on the solid phase support, or the radiolabeled indicator antibody, to yield false positive or false negative results. The selection of "blockers" therefore may add substantially to the specificity of the assays described in the present invention.

It has been found that a number of nonrelevant (i.e., nonspecific) antibodies of the same class or subclass (isotype) as those used in the assays (e.g., IgG1, IgG2a, IgM, etc.) can be used as "blockers". The concentration of the "blockers" (normally 1–100 μg/Il) may be important, in order to maintain the proper sensitivity yet inhibit any unwanted interference by mutually occurring cross reactive proteins in the specimen.

Based on the initial discovery of the Pim polymorphism, other platelet polymorphisms which are also risk factors for thrombotic disease can also be identified by a similar method as described herein. For example, GPIIb, the a subunit of the fibrinogen receptor, has at least 3 alleles. GPIIIa has at least 5 other alleles besides the A1 and the A2 forms. GPIba, the von Willebrand factor receptor, has at least 4–5 alleles. GPIa, the collagen receptor, has at least 2 alleles. Genotyping can be performed on any combination of these alloantigens to distinguish "normal" individuals from those at risk for or having a thrombotic disease (e.g., coronary artery disease).

The following examples illustrate the manner in which the invention can be practiced. It is understood, however, that the examples are for the purpose of illustration and the invention is not to be regarded as limited to any of the specific materials or conditions therein.

EXAMPLE 1

The proband was a 36 year-old woman from a kindred (PT1) with premature coronary artery disease, who presented with unstable angina. The patient and her family were enrolled in a longitudinal and prospective investigation of potential atherogenic and thrombogenic risk factors in the siblings of patients with premature coronary artery disease. The patient's medical history was also remarkable for Tetralogy of Fallot, insulin dependent diabetes mellitus, hypertension, and one episode of deep venous thrombosis, at the age of 22. The proband was pre-menopausal and had never smoked cigarettes.

Physical examination discovered a harsh III/VI holosystolic murmur at the left lower sternal border, which radiated to the neck. Laboratory tests revealed a total serum cholesterol of 169 mg/dl, triglycerides of 12 mg/dl, HDL of 36 mg/dl, and LDL of 108 mg/dl. An ECG performed at the time of presentation demonstrated anterior T wave changes consistent with ischemia and incomplete right bundle branch block. Coronary angiography later revealed a single eccentric 70% stenotic lesion in the left anterior descending coronary artery.

In addition to the routine evaluation, various platelet studies were performed. western immunoblots to measure platelet GPIIb-IIIa revealed that the platelets of two family members reacted with low affinity with a monoclonal antibody (SZ21) (Immunotech, Westbrook, Me.; Weiss, et al., Tissue Antigens, 4:374, 1995) specific for GPIIIa. It was determined that the abnormal reactivity was related to the presence of the uncommon $Pl^{A2}$ variant of the $Pl^A$ platelet alloantigen system.

Family history revealed that the proband had multiple other relatives with premature coronary artery disease. Genotypic analysis of the living members of PT1 demonstrated that seven of eight members where $Pl^{A2}$ positive, including all four affected members; the one $Pl^{A2}$ negative member had no evidence of coronary heart disease. A pedigree constructed for kindred PT1 based on the medical records of all living members, as well as their Pln status is presented in FIG. 1.

EXAMPLE 2

Studies based on patient and control subjects were conducted at the Johns Hopkins University and Hospital under approval by the Joint Committee for Clinical Investigation to obtain genotypic analyses. Genotypic analysis were performed on seventy-one consecutive case subjects admitted to the Coronary Care Unit of the Johns Hopkins Hospital with an established diagnosis of myocardial infarction or unstable angina as defined by the World Health Organization criteria. Similar genotypic analyses were performed on control subjects matched with the case subjects for age, race, and gender, but who had no documented history of either stable or unstable angina or myocardial infarction. The control subjects were selected by reviewing patient charts from a population of patients admitted to the general medical and intensive care services of the Johns Hopkins Hospital. Sixty-eight consecutive subjects who fulfilled these criteria were selected.

Determination of $Pl^A$ genotypes. Genomic DNA was isolated from 200 microliters of whole blood, as previously described (P. F. Bray et al., *Blood* 84:4361–7, 1994), or using the QIAamp Blood Kite™ (Qiagen, Chatsworth, Calif.), according to the manufacturer's instructions. In the former procedure whole blood (0.5 mL) was added to an equal volume of PCR lysis buffer (PLB; 0.32 mol/L sucrose, 20 mmol/L Tris [pH 7.5), 1% Triton X-100, 5 mmol/L $MgCl_2$). Samples were centrifuged for 20 seconds at 13,000× g, the pellet was resuspended in 1 mL PLB, and this process was repeated two times. The pellet was resuspended in 0.5 mL of SIB (50 mmol/L KCl, 10 mmol/L Tris [pH 8.3], 2.5 mmol/L gelatin, 0.45% NP-40, 0.45% Tween 20) plus 4 mg/mL proteinase K and incubated at 65° C. for one hour. The sample was then boiled for 20 minutes to inactivate the proteinase K and stored at −20° C. Twenty-five microliters of lysate was equivalent to approximately 1 g of genomic DNA.

To detect the T to C base substitution responsible for the $Pl^{A2}$ polymorphism at base 1565 in exon 2 of the GPIIIa gene, two procedures were used: (1) reverse dot blot hybridization and (2) allele-specific restriction digestion. The exon numbering and nucleotide sequence used were those according to A. B. Zimrin et al. (*J. Biol. Chem.* 2:8590–5, 1990).

In the first technique, exon 2 was amplified from patient or control genomic DNA in a polymerase chain reaction (PCR) using the primers as shown in SEQ ID NO:1 and SEQ ID NO:2, below, flanking the exon (previously described by Y.Jin et al., *Blood* 82:2281–8, 1993, which description is incorporated herein by reference in its entirety).

5'-CCTGCCTCTGGGCTCAC-3' (SEQ ID NO:1)
5'-TGCCTCCGGGCTCACC-3' (SEQ ID NO:2)

Figure 3A:
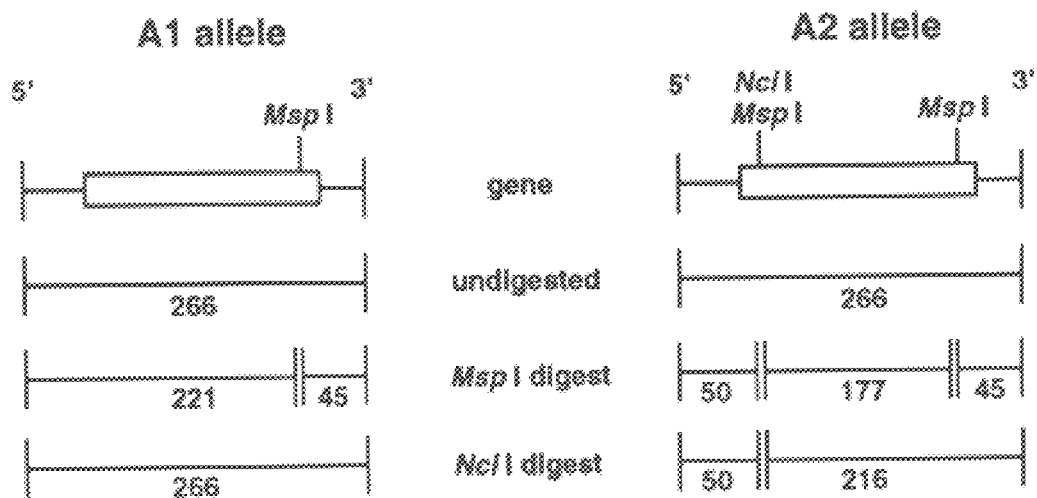
FIGS. 3A, 3B and 3C represent the results of genotyping of patient $Pl^A$ loci by allele-specific restriction digestion and reverse dot blot hybridization.
Figure 3B:
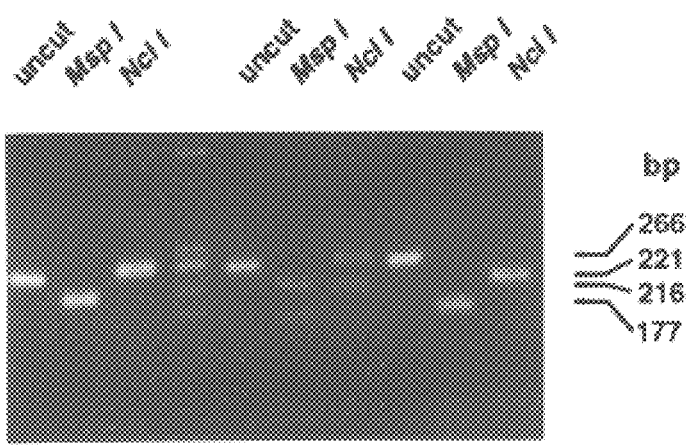

The restriction enzymes MspI and NciI (New England Biolabs, Beverly, Mass.) were able to distinguish the $Pl^{A1}$ from the $Pl^{A2}$ allele because new MspI and NciI recognition sites are generated as the result of the T to C nucleotide substitution ($Pl^{A1}$ to $Pl^{A2}$) at position 1565 of the GPIIIa gene. The PCR products of exon 2 were digested separately with both enzymes, and the resulting fragments were analyzed on a 3% agarose gel. FIG. 3A is a restriction map of GPIIIa exon 2, undigested fragments and digestion products resulting when PCR products are digested with the restriction enzymes MspI and NciI. Vertical bars indicate the ends of PCR fragments or digestion products. For clarity and because it does not cause a detectable change in the fragment sizes, an additional MspI site (present in both PlA alleles) 7 base pairs from the 3' MsPI site is not shown. FIG. 3B is a photograph of a representative ethidium stained 3% agarose gel showing PCR products for patients corresponding to the three possible allelic combinations $Pl^{A1/A1}$, $Pl^{A1/A2}$, and $Pl^{A2/A2}$, Undigested DNA (lanes 1, 5, 8), MMPI digested (lanes 2, 6, 9), and NciI digested (lanes 3, 7, 10) PCR products from patient DNA corresponding to the three possible allelic combinations: $Pl^{A1/A1}$ (lanes 1 to 3), PlA1/A2 (lanes 5–7), and PlA2/A2 (lanes 8–10). Lane 4 contains ΦX174 DNA cut with HaeIII as a size marker.

Figure 3C:
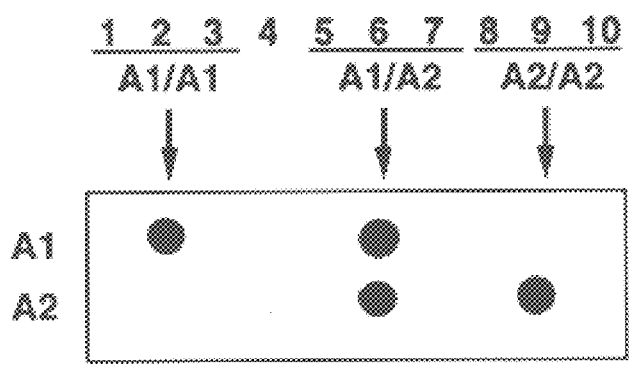

In a second method of analysis, oligonucleotides specific for either the $Pl^{A1}$ or $Pl^{A2}$ allele were used in a reverse dot blot hybridization reaction as described in P. F. Bray et al., supra, 1994, which is incorporated herein in its entirety. Briefly, PCR oligonucleotides were designed from published genomic DNA sequences and synthesized on an Applied Biosystems (Foster City, Calif.) DNA synthesizer. Amino-linked allele-specific oligonucleotides (ASOs), SEQ ID NO:3 and 4, differed by the single nucleotide that has been shown to cause the polymorphic amino acid. Amino groups and biotin (Applied Biosystems) were added to the 5' end of the appropriate oligonucleotide. Each biotinylated primer pair amplified a fragment of 200 to 300 bp of genomic DNA containing the polymorphic site responsible for the amino acid substitution causing a given platelet alloantigen. Specificity of oligonucleotide priming was confirmed by the ability to produce a single PCR fragment on an agarose gel. Results of the reverse dot blot hybridization using the same patient material as in FIG. 3B is shown in FIG. 3C. Filters are shown with $Pl^{A1}$ allele specific oligonucleotides on the top; PlA2, on the bottom.

Membrane preparation. Biodyne C membranes (Pall Biosupport, East Hills, N.Y.) were rinsed in 0.1 N HCl, rinsed in water, incubated in 10% (0.52 mol/L) EDC for 15 minutes, at room temperature, rinsed in water and allowed to air dry. Amino-linked ASOs were diluted to 5 pmol/L/AL with 0.5 mol/L $NaHCo_3/Na_2CO_3$ buffer, pH 8.4, and 2 μL was carefully applied to a filter and allowed to dry for 15 minutes. Membranes were then rinsed once in 0.1 N NaOH for 1 minute, rinsed three times in water, and allowed to dry. This procedure covalently linked the ASOs to the filter. The filters can be stored at room temperature for at least 6 months.

Hybridizing and washing. Two hundred nanograms of genomic DNA was amplified in a 50 μL PCR reaction with the biotinylated primers as described in Y. Jin, supra. A positive control DNA for each antigen system was used. For each set of PCR primers, a negative control consisting of no template DNA in the PCR reaction was always performed to assure no products were amplified from potentially contaminating DNA. In some cases, two or three primer pairs were used in a single PCR reaction. Twenty-five to thirty microliters of each PCR reaction from a single individual was added to 15 mL 2X SSC(LX S.C.=150 mmol/L NaCl/15 mmol/L trisodium citrate, pH 7.0)/0.1% sodium dodecyl sulfate (SDS) in a polypropylene tube. The membrane was added, the tube was boiled for 5 minutes to denature the PCR products, and the tube was immediately transferred to a shaking 45° C. water bath for 1 hour or more. Filters were washed in 40 mL of 0.5X S.C./0.1% SDS at 42° C. for 10 minutes. Multiple filters from different individuals were washed in one tube. The wash buffer was poured off and the filters were incubated with 5 μL of streptavidin-horseradish peroxidase conjugate in 20 mL of 2X S.C./0.1% SDS for 15 minutes at room temperature. The strips were then washed three times for 2 minutes in 2XSSC/0.1% SDS and two times in 0.1 mol/L NaCitrate, pH 5.0, for 2 minutes. Color was detected with 10 μL $H_2O_2$ added to 20 mL of 0.1 mg/mL TMB in 0.1 mol NaCitrate, pH 5.0.

Figure 2:
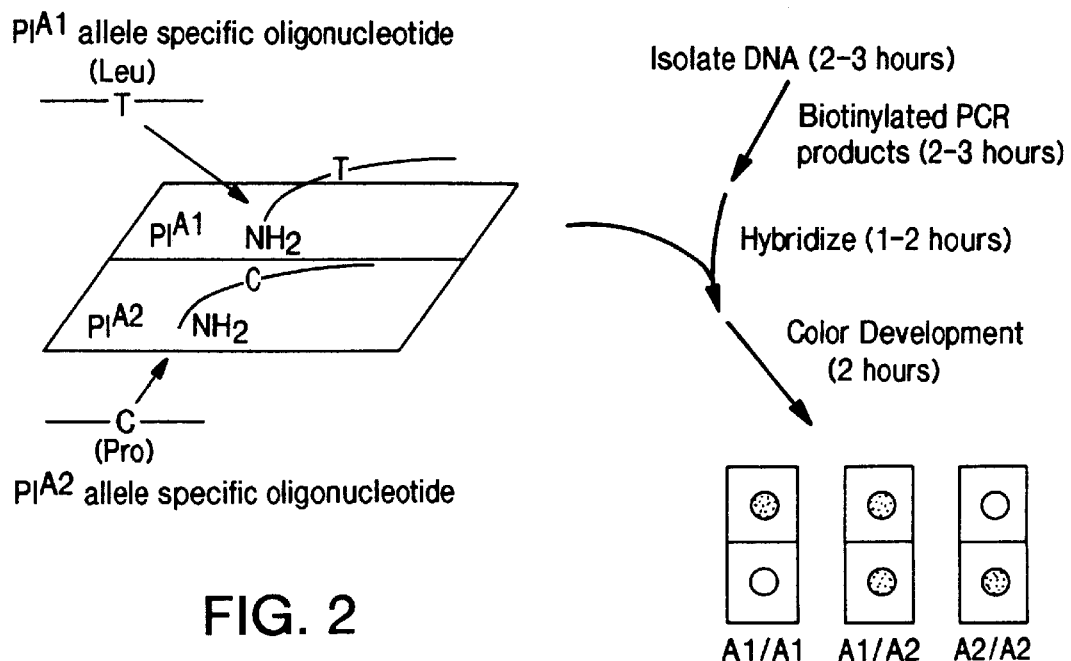
FIG. 2 shows a schematic representation of the reverse dot blot procedure.

For the reverse dot blot hybridization reactions, oligonucleotides specific for either the $Pl^{A1}$ or $Pl^{A2}$ allele were covalently attatched to filters hybridized with biotinylated GPIIIa exon 2 PCR-products, and reactivity detected by an enhanced chemiluminescence technique as described (Kim, et al., *Transfusion* 3:863, 1995; Bray, et al., *Blood*, 84:4361, 1994). FIG. 2 shows a schematic diagram of the reverse dot blot procedure.

Statistical analyses. The size of the sample was determined after pilot studies in the case series indicated that prevalence of $Pl^{A2}$ would approximate 40%, and the expected prevalence in a control series would not exceed 20%. With the anticipation that a difference of this magnitude would support strongly the concept that $Pl^{A2}$ is a significant genetic risk factor, and accepting a one side α-error of 0.05, the size of the sample was set at 71 to limit the β-error to 0.1. The case and control groups were compared for established coronary heart disease risk factors by the Student's t-test (for the continuous variables, two-tailed), using 0.05 as a criterion for statistical significance of observed differences. Discrete data (including $Pl^A$) were analyzed by the chi-square test. The strength of association of the $Pl^{A2}$ genetic factor with the occurrence of acute coronary events was estimated by calculation of the odds ratios using the Epi Info 6 and Cornfield methodology for calculation of 95% confidence limits. The relative strength of association of other risk factors was measured in similar manner. The significance of the difference in the odds ratios was not tested, as the sample size was not designed to carry out such analyses. The relation of the PlA allele to each of the remaining predictor variates was examined by bivariate Chi-square analysis. Finally, the association of the $Pl^{A2}$ allele with coronary events, standardized for other risk factors, was determined by the multiple logistic regression method using Stata version 4.0.

Characteristics of the study population. Demographic data were obtained from all cardiac patients, and included the current age, age at first event, gender, smoking history, blood pressure, total cholesterol, history of diabetes, level of physical activity, and history of previous coronary or cerebral ischemic event. The two groups were matched according to age, race, and gender and therefore, no significant differences were observed for these variables. Owing to the sample size, the coronary heart disease risk factors did not differ significantly between case and control groups, except for smoking (P=0.05). The results of the demographic study are shown in Table 2 below:

TABLE 2

Characteristics of Cases and Controls for Selected Coronary Heart Disease Risk Factors

| Risk Factor | Cases | Controls | P* |
|---|---|---|---|
| Number | 71 | 68 | |
| Age† | 56.3 ± 12.8 | 58.3 ± 14.3 | 0.39 |
| Gender % Male | 70 | 69 | 0.99 |
| Blood Pressure % Hypertension: | 52 | 37 | 0.10 |
| Smoking % Present of Pass§ | 72 | 55 | 0.05 |
| Total Blood Cholesterol % ≧200 mg/dl¶ | 26 | 22 | 0.69 |
| Diabetes % positive∫ | 18 | 22 | 0.73 |

*T test (continuous variable) and chi-square test (discrete variables) for difference in risk factor frequency between cases and controls.
†Mean in Years ± S.D.; for cases, age is of onset, not current.
‡Defined as systolic blood pressure ≧ 140 mm Hg at time of admission to hospital.
§Documented history of present or past cigarette smoking.
¶On admission; to convert values for cholesterol to millimoles per liter, multiply by 0.026.
∫Documented history of type I or type II Diabetes Mellitus.

Prevalence of $Pl^{A2}$ in patients with MI/USA and in controls.

Representative genotyping results for three of the seventy-one cases are shown in FIG. 3, demonstrating the three possible $Pl^A$ allelic combinations. Table 3 summarizes the genotyping data for all cases and controls. The prevalence of $Pl^{A2}$ positive patients in the seventy-one case subjects was 39.4 percent (percentage of subjects that were either heterozygous A1/A2 or homozygous A2/A2). This is significantly higher than the prevalence of $Pl^{A2}$ and coronary events is even stronger in individuals less than 60 years of age at first event. Of the 42 cases less than 60 years of age at onset of disease, 50 percent carried at least one $Pl^{A2}$ allele as compared to 13.8 percent among the controls less than sixty years of age (P=0.002).

TABLE 3

Frequency of $P1^{A2}(-)*$ (and $P1^{A2}(+)$†Subjects Among Cases and Controls (all ages and age less than 60 years)‡

| Genotype | Cases (%) | Controls (%) | P§ |
|---|---|---|---|
| All Ages | | | |
| A1/A1 | 43(60.6) | 55(80.9) | |
| A1/A2 + A2/A2 | 23 + 5(39.4) | 12 + 1(19.1) | 0.01 |
| Total | 71(100) | 68(100) | |
| Age ≦60 Years | | | |
| A1/A1 | 21(50) | 31(86.2) | |
| A1/A2 + A2/A2 | 19 + 2(50) | 5 + 0(13.8 | 0.02 |
| Total | 42(100) | 36(100) | |

*Genotype = $P1^{A1/A1}$.
†Genotype = $P1^{A1/A2}$ or $P1^{A2/A2}$.
‡For cases, age is of onset, not current.
§Chi-square test for difference in $P1^{A2}$ prevalence among cases and controls.

Comparison of Major Coronary Heart Disease Risk Factors Between Cases and Controls.

Among the major risk factors for coronary heart disease examined in this study, the risk factor associated with the highest estimated odds ratio (±95 percent confidence interval) was the $Pl^{A2}$ allele [2.8 (1.20 to 6.40)], followed in order by smoking [2.2 (1.01 to 4.79)], hypertension [1.9 (0.90 to 3.94)], and hypercholesterolemia (total serum cholesterol greater than 200 mg per deciliter [5.2 mmol per liter])[1.3(0.54–3.00)] (Table 3). The prevalence of diabetes mellitus was similarly high among study and control subjects. As anticipated, the odds ratios for each of the risk factors, including PlA2, were higher in the subjects less than sixty years of age when compared to the entire population. In this subset of subjects less than 60 years of age, the risk factor associated with the highest estimated odds ratio was again the $Pl^{A2}$ allele [6.2(1.82 to 22.4)], followed in order by smoking [3.8(1.22 to 12.0)], hypercholesterolemia [3.7(0.81 to 18.7)], and hypertension [2.1(0.73 to 5.90) (Table 4).

A multiple logistic regression model adjusting for smoking, hypertension, hypercholesterolemia, and age greater than 60 years provided an odds ratio of 3.3 (1.39 to 7.69), for the relationship between acute coronary events and the $Pl^{A2}$ allele. This is consistent with the finding that the bivariate association of the allele with smoking, hypertension, hypercholesterolemia, and age greater than 60 years was uniformly not statistically significant.

The data show that there is a strong association between $Pl^{A2}$ positivity and the occurrence of acute coronary events. There is a statistically significant increase in the prevalence of individuals with at least one $Pl^{A2}$ allele [$Pl^{A2}(+)$] in study subjects with either myocardial infarction or unstable angina as compared to a matched control group selected for the absence of such events.

TABLE 4

| | | Odds Ratios for Selected Risk Factors | | | | | |
|---|---|---|---|---|---|---|---|
| | | All Ages* | | | Age <60 Years* | | |
| Risk Factor | Class | Cases | Controls | Odds Ratio (95% Cl) | Cases | Controls | Odds Ratio (95% Cl) |
| P1A Genotype | A2(+)† | 28 | 13 | 2.8(1.20–6.40) | 21 | 5 | 6.2(1.82–22.4) |
| | A2(–) | 43 | 55 | | 21 | 31 | |
| Smoking | Now/Past‡ | 50 | 30 | 2.2(1.01–4.79) | 32 | 18 | 3.8(1.22–12.0) |
| | Never | 19 | 30 | | 8 | 17 | |
| Systolic Blood Pressure | ≧140 mm Hg§ | 36 | 25 | 1.9(0.90–3.94) | 19 | 11 | 2.1(0.73–5.9) |
| | <140 mm Hg§ | 33 | 43 | | 21 | 25 | |
| Total Blood Cholesterol | ≧200 mg/dl§ | 18 | 15 | 1.3(0.54–3.00) | 10 | 3 | 3.7(0.81–18.7) |
| | <200 mg/dl§ | 50 | 53 | | 30 | 33 | |
| Diabetes | N/1DDM¶ | 13 | 15 | 0.8∫ | 8 | 8 | 0.8∫ |
| | None | 58 | 53 | | 34 | 28 | |

*For cases, age is of onset, not current.
†Genotype = $P1^{A1/A2}$.
‡Documented history of present or past cigarette smoking.
§On Admission; to convert values for cholesterol to millimoles per liter, multiplying by 0.026.
¶Documented history of type I or type II Diabetes Mellitus.
∫Not calculated; see discussion for explanation.

EXAMPLE 3

Other platelet polymorphisms that can be used as risk factors for thrombotic disease include the following:

GPIIb, the α subunit of the fibrinogen receptor, has at least 3 alleles. GPIIIa has at least 5 other alleles besides the A1 and the A2 forms. GPIbα, the von Willebrand factor receptor, has at least 4–5 alleles. GPIa, the collagen receptor, has at least 2 alleles. Genotyping can be performed on all of these alloantigens to distinguish "normal" individuals from those at risk for or having a thrombotic disease (e.g., coronary artery disease).

The patients who were used in the $Pl^A$ studies in the above examples, were also studied for differences between "normals" and patients in the above-identified markers. The alloantigen known as "Bak" of GPIIb showed some difference between normals and patients. The "Pen" allele of GPIIIa was also studied. Genotyping on the alloantigen known as "Ko" (of Von Willebrand factor) was performed. "Length polymorphisms" are also examined. Genotyping was performed on "Br" alloantigen (collagen receptor) as well. Combinations of any or all of these exemplary or other platelet antigens can be examined for differences between "normals" and "at risk" patients.

The foregoing description of the invention is exemplary for purposes of illustration and explanation. It should be understood that various modifications can be made without departing from the spirit and scope of the invention. Accordingly, the following claims are intended to be interpreted to embrace all such modifications.

What is claimed is:

1. A method for diagnosing a subject having or at risk of having a thrombotic disease comprising:

contacting a target nucleic acid isolated from a specimen of a subject with a reagent that detects a $Pl^{A2}$ polymorphism in the GPIIIa gene; and detecting the presence or absence of the $Pl^{A2}$ polymorphism, wherein the presence of the polymorphism is indicative of a thrombotic disease.

2. The method of claim 1, wherein the target nucleic acid is DNA.

3. The method of claim 1, wherein the target nucleic acid is RNA.

4. The method of claim 1, wherein the reagent is a nucleic acid probe.

5. The method of claim 4, wherein the probe is detectably labeled.

6. The method of claim 5, wherein the label is selected from the group consisting of a radioisotope, a bioluminescent compound, a chemiluminescent compound, a fluorescent compound, a metal chelate, and an enzyme.

7. The method of claim 1, wherein the target nucleic acid is amplified prior to detection.

8. The method of claim 7, wherein the amplifying is by polymerase chain reaction (PCR).

9. The method of claim 1, wherein the target nucleic acid has a nucleotide sequence selected from the group consisting of 5'-CCTGCCTCTGGGCTCAC-3' (SEQ ID NO:1) and

5'- TGCCTCCGGGCTCACC-3'(SEQ ID NO:2).

10. The method of claim 4, wherein the nucleic acid probe has the sequence selected from the group consisting of 5'- GTGAGCCCAGAGGCAGG-3' (SEQ ID NO:3) and

5'-GGTGAGCCCGGAGGCA-3' (SEQ ID NO:4).

11. The method of claim 1, wherein the reagent is a restriction endonuclease.

12. The method of claim 11, wherein the restriction endonuclease includes a recognition site C↓(G/C)GG.

13. The method of claim 12, wherein the restriction endonuclease is NciI or MspI.

14. The method of claim 1, wherein the specimen is blood.

15. The method of claim 1, wherein the thrombotic disease is selected from the group consisting of coronary heart disease (CHD), premature stroke, coronary artery thrombosis, myocardial infraction, cerebrovascular disease, unstable angina, and restenosis.

16. The method of claim 1, wherein the polymorphism is a heterozygous mutation.

17. The method of claim 1, wherein the polymorphism is a homozygous mutation.

18. The method of claim 1, wherein the contacting is by reverse dot blot hybridization.

19. The method of claim 1, wherein the subject is human.

20. The method of claim 19, wherein the subject is 60 years of age or less.

* * * * *

```
                          SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..17

(xi) SEQUENCE DESCRIPTION: SEQ ID NO:1:

CCTGCCTCTG GGCTCAC                                                      17

(2) INFORMATION FOR SEQ ID NO:2:

(i) SEQUENCE CHARACTERISTICS:
             (A) LENGTH: 16 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..16

(xi) SEQUENCE DESCRIPTION: SEQ ID NO:2:

TGCCTCCGGG CTCACC                                                       16

(2) INFORMATION FOR SEQ ID NO:3:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (A) NAME/KEY: CDS
             (B) LOCATION: 1..17

(xi) SEQUENCE DESCRIPTION: SEQ ID NO:3:

GTGAGCCCAG AGGCAGG                                                      17

(2) INFORMATION FOR SEQ ID NO:4:

(i) SEQUENCE CHARACTERISTICS:
             (A) LENGTH: 16 base pairs
```

```
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..16

(xi) SEQUENCE DESCRIPTION: SEQ ID NO:4:

GGTGAGCCCG GAGGCA                                                    16

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..22

(xi) SEQUENCE DESCRIPTION: SEQ ID NO:5:

TTCTGATTGC TGGACTTCTC TT                                             22

(2) INFORMATION FOR SEQ ID NO:6:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..22

(xi) SEQUENCE DESCRIPTION: SEQ ID NO:6:

TCTCTCCCCA TTGGCAAAGA GT                                             22
```